(12) United States Patent
Simpson et al.

(10) Patent No.: US 7,608,628 B2
(45) Date of Patent: Oct. 27, 2009

(54) ALKYLSULPHONAMIDE QUINOLINES

(75) Inventors: Thomas R. Simpson, West Chester, PA (US); James Kang, Chadds Ford, PA (US); Jeffrey S. Albert, Wilmington, DE (US); Cristobal Alhambra, Havertown, PA (US); Gerald M. Koether, Bear, DE (US); James Woods, Wilmington, DE (US); Yan Li, Glen Mills, PA (US)

(73) Assignee: AstraZeneca AB, Sodertalje (SE)

( * ) Notice: Subject to any disclaimer, the term of this patent is extended or adjusted under 35 U.S.C. 154(b) by 14 days.

(21) Appl. No.: 11/609,166

(22) Filed: Dec. 11, 2006

(65) Prior Publication Data
US 2008/0021062 A1    Jan. 24, 2008

Related U.S. Application Data

(60) Provisional application No. 60/749,431, filed on Dec. 12, 2005, provisional application No. 60/821,016, filed on Aug. 1, 2006.

(51) Int. Cl.
C07D 215/38 (2006.01)
A61K 31/47 (2006.01)
A61P 1/00 (2006.01)
A61P 35/00 (2006.01)
A61P 37/00 (2006.01)
A61P 5/00 (2006.01)
A61P 9/00 (2006.01)

(52) U.S. Cl. .................................. 514/313; 546/159
(58) Field of Classification Search .................. None
See application file for complete search history.

(56) References Cited

U.S. PATENT DOCUMENTS

| | | | |
|---|---|---|---|
| 5,177,096 A | 1/1993 | Keenan et al. | |
| 5,248,689 A | 9/1993 | Girard et al. | |
| 5,444,081 A | 8/1995 | Gleason et al. | |
| 5,686,455 A | 11/1997 | Adams et al. | |
| 5,811,553 A | 9/1998 | Farina et al. | |
| 5,942,523 A | 8/1999 | Bichon et al. | |
| 6,057,362 A | 5/2000 | Yamashita | |
| 6,232,342 B1 | 5/2001 | Carr et al. | |
| 6,277,862 B1 | 8/2001 | Giardina et al. | |
| 6,387,898 B1 | 5/2002 | Feuerstein et al. | |
| 6,608,083 B1 | 8/2003 | Farina et al. | |
| 6,743,804 B2 | 6/2004 | Giardina et al. | |
| 6,858,630 B2 | 2/2005 | Luengo et al. | |
| 7,253,286 B2 | 8/2007 | Funahashi et al. | |
| 2003/0195204 A1 | 10/2003 | Giardina et al. | |
| 2004/0006135 A1 | 1/2004 | Sobolov-Jaynes et al. | |
| 2007/0254886 A1 | 11/2007 | Habashita et al. | |

FOREIGN PATENT DOCUMENTS

| EP | 1192952 | 4/2002 |
|---|---|---|
| EP | 0804419 | 8/2003 |
| EP | 0940391 | 8/2004 |
| WO | 9532948 A1 | 12/1995 |
| WO | 9602509 A1 | 2/1996 |
| WO | 97/19927 | 6/1997 |
| WO | 97/21680 | 6/1997 |
| WO | 9719926 A1 | 6/1997 |
| WO | WO 9719928 | 6/1997 |
| WO | WO 9951565 | 10/1999 |
| WO | WO 0012497 | 3/2000 |
| WO | 0031037 A1 | 6/2000 |
| WO | 0064877 A1 | 11/2000 |
| WO | WO 0213825 | 2/2002 |
| WO | 0238548 A1 | 5/2002 |
| WO | WO 02094187 | 11/2002 |
| WO | 2004000355 | 12/2003 |
| WO | 2004050626 | 6/2004 |
| WO | 2004050627 | 6/2004 |
| WO | WO 2004087153 | 10/2004 |
| WO | WO 2005014532 | 2/2005 |
| WO | WO 2005014533 | 2/2005 |
| WO | WO 2005014534 | 2/2005 |
| WO | WO 2005094801 | 10/2005 |
| WO | WO 2005108359 | 11/2005 |
| WO | 2006/050991 | 5/2006 |
| WO | 2006/120478 | 11/2006 |
| WO | WO 2006/137789 | 12/2006 |
| WO | WO 2007022059 | 2/2007 |

(Continued)

OTHER PUBLICATIONS

Giardina et al.: Discovery of a novel class of selective non-peptide antagonists for the human neurokinin-3 receptor. 2. Identification of (S)-(N)-(1-phenylpropyl)-3-hydroxy-2-phenylquinoline-4-carboximide (SB 223412). J Med Chem, 42:1053-1065, 1999.*

(Continued)

*Primary Examiner*—Brian-Yong S Kwon
*Assistant Examiner*—Bong-Sook Baek
(74) *Attorney, Agent, or Firm*—Kenneth F. Mitchell

(57) ABSTRACT

Compounds of Formula II

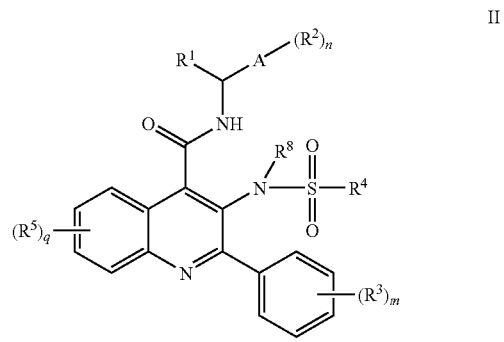

wherein $R^1$, A, $R^2$, $R^3$, $R^4$, $R^5$, $R^8$, n, m and q are as described in the specification, pharmaceutically-acceptable salts, methods of making, pharmaceutical compositions containing and methods for using the same.

2 Claims, No Drawings

FOREIGN PATENT DOCUMENTS

WO    2008021388    2/2008

OTHER PUBLICATIONS

Wolff, Manfred E.: Burger's Medicinal Chemistry and Drug Discovery, 5ed. Part I. John Wiley & Sons, p. 975-977, 1995.*

Banker et al.: Modern Pharmaceutics. 3ed. Marcel Dekker, Inc., New York, p. 451 and p. 596, 1996.*

Jeffrey S. Albert, "Neurokinin antagonists and their potential role in treating depression and other stress disorders," Expert Opin. Ther. Patents, 14(10), pp. 1421-33 (2004).

Jeffrey S. Albert, et. al., "Neurokinin-3 receptor antagonists in schizophrenia", Expert Opin. Ther. Patents, 16 (7), pp. 925-937 (2006).

Giardina, et al., Discovery of a novel Class of Selective Non-Peptide Antagonists for the Human Neurikinin-3Receptor. 2. Identification of (S)-N-(1-Phenylpropyl)-3-Hydroxy-2-Phenylquinoline-4-Carboxamide (SB 223412), Journal of Med. Chem., 1999, vol. 42, pp. 1053-1065.

Memorandum dated Apr. 6, 2006 regarding US Patent No. 6,608,083 which was filed May 25, 1995.

* cited by examiner

ALKYLSULPHONAMIDE QUINOLINES

RELATED APPLICATIONS

This application claims the benefit under 35 U.S.C. § 119 (e)(1) of Provisional Applications 60/749,431 filed Dec. 12, 2005 and 60/821,016 filed Aug. 1, 2006.

FIELD OF THE INVENTION

This invention relates to quinoline derivatives, pharmaceutical compositions comprising them, and the use of such compounds in the treatment of central nervous system and peripheral diseases or disorders. This invention also relates to the use of such compounds in combination with one or more other CNS agents to potentiate the effects of the other CNS agents. The compounds of this invention are also useful as probes for the localization of cell surface receptors.

BACKGROUND OF THE INVENTION

Tachykinin receptors are the targets of a family of structurally related peptides that include substance P (SP), neurokinin A (NKA) and neurokinin B (NKB), collectively "tachykinins." Tachykinins are synthesized in the central nervous system (CNS), and peripheral tissues, where they exert a variety of biological activities. Three tachykinin receptors are known which are named neurokinin-1 (NK-1), neurokinin-2 (NK-2) and neurokinin-3 (NK-3) receptors. NK-1 and NK-2 receptors are expressed in a wide variety of peripheral tissues and NK-1 receptors are also expressed in the CNS whereas NK-3 receptors are primarily expressed in the CNS.

The neurokinin receptors mediate a variety of tachykinin-stimulated biological effects that include: transmission of excitatory neuronal signals in the CNS and periphery (e.g. pain signals), modulation of smooth muscle contractile activity, modulation of immune and inflammatory responses, induction of hypotensive effects via dilation of the peripheral vasculature, and stimulation of endocrine and exocrine gland secretions.

In the CNS, activation of NK-3 receptors has been shown to modulate dopamine, acetylcholine and serotonin release, suggesting a therapeutic utility for NK-3 ligands for the treatment of a variety of disorders including anxiety, depression, schizophrenia and obesity. Studies in primate brain have shown the presence of NK-3 mRNA in a variety of regions relevant to these disorders. Studies in rats have shown NK-3 receptors to be located on MCH-containing neurons in the lateral hypothalamus and zona incerta, again suggesting a therapeutic utility for NK-3 ligands for obesity.

Non-peptide ligands have been developed for each of the tachykinin receptors, however known non-peptide NK-3 receptor antagonists suffer from a number of problems such as species selectivity which limits the potential to evaluate these compounds in many appropriate disease models. New non-peptide NK-3 receptor ligands are therefore desirable for use as therapeutic agents and as tools to investigate the biological consequences of NK-3 receptor modulation.

SUMMARY OF THE INVENTION

Disclosed are compounds, particularly alkylsulfonamide quinoline derivatives with affinity for NK-3 receptors (NK-3r). These compounds have potential for the treatment of a broad array of diseases, disorders and conditions including but not limited to depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer in which modulation of the activity of NK-3 receptors is beneficial.

Ligands for NK-3 receptors disclosed and stereoisomers, enantiomers, in vivo-hydrolysable precursors and pharmaceutically acceptable salts thereof are compounds of Formula I,

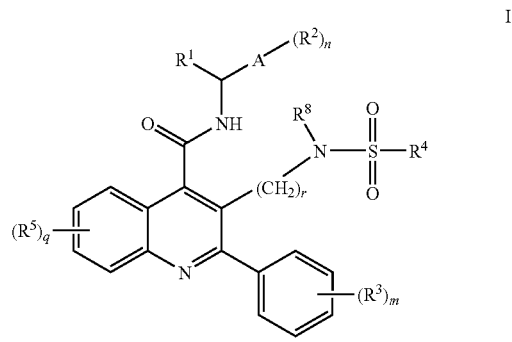

wherein:
$R^1$ is selected from H, $C_{1-4}$alkyl-, $C_{3-6}$cycloalkyl- and $C_{1-4}$alkylOC(O)—;

A is phenyl or $C_{3-7}$cycloalkyl-;

$R^2$ at each occurrence is independently selected from H, —OH, —NH$_2$, —CN, halogen, $C_{1-6}$alkyl-, $C_{3-7}$cycloalkyl-, $C_{1-6}$alkoxy- and $C_{1-6}$alkoxy$C_{1-6}$alkyl-;

n is 1, 2 or 3;

$R^3$ at each occurrence is independently selected from H, —OH, —NH$_2$, —NO$_2$, —CN, halogen, $C_{1-6}$alkyl-, $C_{1-6}$alkoxy- and $C_{1-6}$alkoxy$C_{1-6}$alkyl-;

m is 1, 2 or 3;

r is 0, 1, 2 or 3, $R^4$ is selected from $C_{1-4}$alkyl-, $C_{1-6}$alkoxy$C_{1-6}$alkyl-, $C_{3-7}$cycloalkyl- and E—(CH$_2$)$_p$—, where E is selected from —NR$^6$R$^7$, —SR$^6$, —SOC$_{1-6}$alkyl, —SO$_2$C$_{1-6}$alkyl, N$^+$(O$^-$)R$^6$R$^7$, —NR$^6$SO$_2$R$^7$, aryl and an N- or C-linked 5- or 6-membered aromatic or non-aromatic heterocyclic ring having 1, 2, 3 or 4 nitrogen atoms or an N-oxide thereof and p is 0, 1, 2, 3, 4 or 5;

$R^5$ at each occurrence is independently selected from H, —OH, —CN, halogen, —R$^6$, —OR$^6$—NR$^6$R$^7$, —SR$^6$, —SOR$^6$ and —SO$_2$R$^6$;

q is 1, 2 or 3;

wherein:
$R^6$ and $R^7$ at each occurrence are independently selected from H, a $C_{1-6}$ straight or branched alkyl group, a $C_{2-6}$ straight or branched alkenyl or alkynyl group and a $C_{3-7}$-carbocyclic group having zero, one or two double- or triple-bonds, wherein said groups are either unsubstituted or substituted with one or more moieties selected from —OH, =O, —NH$_2$, —CN, halogen, aryl and $C_{1-3}$alkoxy-;

$R^8$ is selected from H, a $C_{1-5}$ straight or branched alkyl group or a $C_{3-5}$ cycloalkyl group wherein said groups are either unsubstituted or substituted with one or more moieties selected from —OH, =O, —NH$_2$, —CN, halogen, aryl and $C_{1-3}$alkoxy-;

and, when $R^4$ is E—$(CH_2)_p$— and said E thereof is an N or C linked 5- or 6-membered aromatic or non-aromatic heterocyclic ring or an N-oxide thereof, said E is unsubstituted or has 1, 2 or 3 substituents independently selected from —OH, =O, —NH$_2$, —CN, halogen, $C_{1-4}$alkyl-, $C_{1-4}$alkoxy-, $C_{1-4}$alkyl-CO—, —NR$^6$R$^7$, aryl and a 5- or 6-membered aromatic or non-aromatic heterocyclic ring having 1, 2, 3 or 4 nitrogen atoms;

and, when $R^1$, $R^2$, $R^3$ or $R^4$ is an alkyl, cycloalkyl, alkoxy or alkoxyalkyl moiety, said moieties are unsubstituted or have 1, 2, 3, 4 or 5 substituents independently selected at each occurrence from —OH, —NH$_2$, —CN, phenyl and halogen.

Also disclosed are pharmaceutical compositions and formulations containing the compounds, methods of using them to treat diseases and conditions either alone or in combination with other therapeutically active compounds or substances, processes and intermediates used to prepare them, uses of them as medicaments, uses of them in the manufacture of medicaments and uses of them for diagnostic and analytic purposes. In particular are disclosed compounds, compositions containing them, and methods using them for treating or preventing conditions and disorders associated with a wide range of diseases or disorders in which NK-3 receptors are considered to have a role.

DETAILED DESCRIPTION OF THE INVENTION

Compounds of the invention are compounds of Formula I,

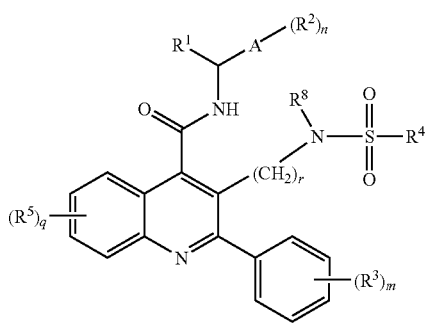

I wherein:

$R^1$ is selected from H, $C_{1-4}$alkyl-, $C_{3-6}$cycloalkyl- and $C_{1-4}$alkylOC(O)—;

A is phenyl or $C_{3-7}$cycloalkyl-;

$R^2$ at each occurrence is independently selected from H, —OH, —NH$_2$, —CN, halogen, $C_{1-6}$alkyl-, $C_{3-7}$cycloalkyl-, $C_{1-6}$alkoxy- and $C_{1-6}$alkoxy$C_{1-6}$alkyl-;

n is 1, 2 or 3;

$R^3$ at each occurrence is independently selected from H, —OH, —NH$_2$, —NO$_2$, —CN, halogen, $C_{1-6}$alkyl-, $C_{1-6}$alkoxy- and $C_{1-6}$alkoxy$C_{1-6}$alkyl-;

m is 1, 2 or 3;

r is 0, 1, 2 or 3, $R^4$ is selected from $C_{1-4}$alkyl-, $C_{1-6}$alkoxy$C_{1-6}$alkyl-, $C_{3-7}$cycloalkyl- and E—$(CH_2)_p$—, where E is selected from —NR$^6$R$^7$, —SR$^6$, —SOC$_{1-6}$alkyl, —SO$_2$C$_{1-6}$alkyl, N$^+$(O$^-$)R$^6$R$^7$, —NR$^6$SO$_2$R$^7$, aryl and an N- or C-linked 5- or 6-membered aromatic or non-aromatic heterocyclic ring having 1, 2, 3 or 4 nitrogen atoms or an N-oxide thereof and p is 0, 1, 2, 3, 4 or 5;

$R^5$ at each occurrence is independently selected from H, —OH, —CN, halogen, —R$^6$, —OR$^6$—NR$^6$R$^7$, —SR$^6$, —SOR$^6$ and —SO$_2$R$^6$;

q is 1, 2 or 3;

$R^8$ is selected from H, a $C_{1-5}$ straight or branched alkyl group or a $C_{3-5}$ cycloalkyl group wherein said groups are either unsubstituted or substituted with one or more moieties selected from —OH, =O, —NH$_2$, —CN, halogen, aryl and $C_{1-3}$alkoxy-;

wherein:

$R^6$ and $R^7$ at each occurrence are independently selected from H, a $C_{1-6}$ straight or branched alkyl group, a $C_{2-6}$ straight or branched alkenyl or alkynyl group and a $C_{3-7}$-carbocyclic group having zero, one or two double- or triple-bonds, wherein said groups are either unsubstituted or substituted with one or more moieties selected from —OH, =O, —NH$_2$, —CN, halogen, aryl and $C_{1-3}$alkoxy-;

and, when $R^4$ is E—$(CH_2)_p$— and said E thereof is an N or C linked 5- or 6-membered aromatic or non-aromatic heterocyclic ring or an N-oxide thereof, said E is unsubstituted or has 1, 2 or 3 substituents independently selected from —OH, =O, —NH$_2$, —CN, halogen, $C_{1-4}$alkyl-, $C_{1-4}$alkoxy-, $C_{1-4}$alkyl-CO—, —NR$^6$R$^7$, aryl and a 5- or 6-membered aromatic or non-aromatic heterocyclic ring having 1, 2, 3 or 4 nitrogen atoms;

and, when $R^1$, $R^2$, $R^3$ or $R^4$ is an alkyl, cycloalkyl, alkoxy or alkoxyalkyl moiety, said moieties are unsubstituted or have 1, 2, 3, 4 or 5 substituents independently selected at each occurrence from —OH, —NH$_2$, —CN, phenyl and halogen;

stereoisomers, enantiomers, in vivo-hydrolysable precursors and pharmaceutically acceptable salts thereof.

Particular compounds are those in accord with Formula II, such compounds being of Formula I wherein r is 0,

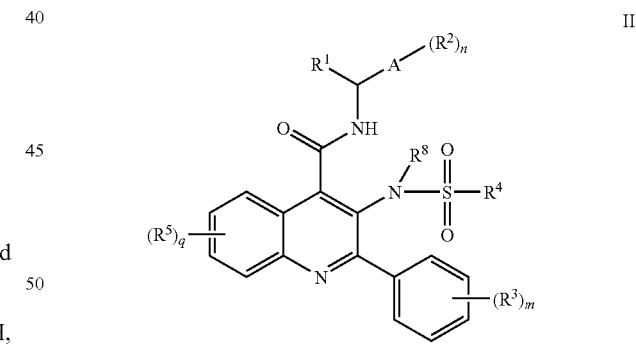

II wherein $R^1$, A, $R^2$, n, $R^3$, m, $R^5$, q, $R^4$, and $R^8$ are as defined for Formula I, in vivo-hydrolysable precursors and pharmaceutically acceptable salts thereof.

Other particular compounds are those of Formula I wherein $R^1$, A, $R^2$, n, $R^3$, m, $R^5$, q, r and $R^8$ are as defined for Formula I, in vivo-hydrolysable precursors and pharmaceutically acceptable salts thereof and wherein $R^4$ is selected from $C_{3-7}$cycloalkyl- and E—$(CH_2)_p$—, where E is selected from —NR$^6$R$^7$, —SR$^6$, —SOC$_{1-6}$alkyl, —SO$_2$C$_{1-6}$alkyl, N$^+$(O$^-$)R$^6$R$^7$, —NR$^6$SO$_2$R$^7$, aryl and an N- or C-linked 5- or 6-membered aromatic or non-aromatic heterocyclic ring having 1, 2, 3 or 4 nitrogen atoms or an N-oxide thereof and p is 1, 2, 3, 4 or 5.

Other particular compounds are those of Formula I wherein $R^1$, A, $R^2$, n, $R^3$, m, $R^5$, q, r and $R^4$ are as defined for Formula I, in vivo-hydrolysable precursors and pharmaceutically acceptable salts thereof and wherein $R^8$ is selected from H, or a $C_{1-5}$ straight or branched alkyl group or a $C_{3-5}$ cycloalkyl group which groups are substituted with one or more moieties selected from —OH, =O, —$NH_2$, —CN, halogen, aryl and $C_{1-3}$alkoxy-.

Other particular compounds are those of Formula I or II wherein A is phenyl.

Other particular compounds are those of Formula II wherein:

A is phenyl;

$R^1$ is selected from $C_{1-4}$alkyl-, $C_{3-6}$cycloalkyl- and $C_{1-4}$alkylOC(O)—;

$R^2$ is selected from H, halogen and unsubstituted $C_{1-6}$alkoxy-;

$R^3$ is H or halogen;

$R^8$ is H or methyl;

n and m are both 1, and when $R^1$ or $R^4$ is an alkyl, cycloalkyl, or alkoxyalkyl moiety, said moieties are unsubstituted or have 1, 2, 3, 4 or 5 substituents independently selected at each occurrence from —OH, —$NH_2$, —CN and halogen, stereoisomers, enantiomers, in vivo-hydrolysable precursors and pharmaceutically acceptable salts thereof.

Other particular compounds are those of Formula II wherein:

A is phenyl;

$R^1$ is selected from $C_{1-4}$alkyl- and $C_{3-6}$cycloalkyl-;

$R^2$ is selected from H, halogen and unsubstituted $C_{1-6}$alkoxy-;

$R^3$ is H or halogen;

$R^8$ is H or methyl;

n and m are both 1;

$R^4$ is selected from $C_{1-4}$alkyl- and E—$(CH_2)_p$—, where E is a substituted or unsubstituted N-linked 5- or 6-membered aromatic or non-aromatic heterocyclic ring having 1, 2, 3 or 4 nitrogen atoms, and $R^5$ is H.

stereoisomers, enantiomers, in vivo-hydrolysable precursors and pharmaceutically acceptable salts thereof.

Still other particular compounds are those of Formula II wherein:

A is phenyl;

$R^1$ is ethyl or cyclopropyl;

$R^2$ is selected from H, F and —$OCH_3$;

$R^3$ is H or F;

$R^8$ is H;

n, m and q are each 1, and $R^5$ at each occurrence is independently selected from H, —OH and halogen, stereoisomers, enantiomers, in vivo-hydrolysable precursors and pharmaceutically acceptable salts thereof.

Still other particular compounds are those in accord with Formula III

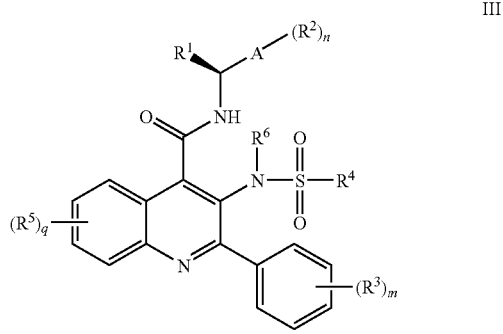

wherein $R^1$, A, $R^2$, n, $R^3$, m, r, $R^4$, $R^5$, $R^8$ and q are as defined for Formula I, in vivo-hydrolysable precursors and pharmaceutically acceptable salts thereof.

Particular compounds are selected from:

3-Methanesulfonylamino-2-phenyl-quinoline-4-carboxylic acid (1-phenyl-propyl)-amide;

3-Ethanesulfonylamino-2-phenyl-quinoline-4-carboxylic acid (1-phenyl-propyl)-amide;

2-Phenyl-3-trifluoromethanesulfonylamino-quinoline-4-carboxylic acid (1-phenyl-propyl)-amide;

2-Phenyl-3-(2,2,2-trifluoro-ethanesulfonylamino)-quinoline-4-carboxylic acid (1-phenyl-propyl)-amide;

2-Phenyl-3-(propane-1-sulfonylamino)-quinoline-4-carboxylic acid (1-phenyl-propyl)-amide;

2-Phenyl-3-(3,3,3-trifluoro-propane-1-sulfonylamino)-quinoline-4-carboxylic acid (1-phenyl-propyl)-amide;

3-Cyclopropanesulfonylamino-2-phenyl-quinoline-4-carboxylic acid (1-phenyl-propyl)-amide;

3-Methanesulfonylamino-2-phenyl-quinoline-4-carboxylic acid (cyclopropyl-phenyl-methyl)-amide;

3-Methanesulfonylamino-2-phenyl-quinoline-4-carboxylic acid [1-(3-fluoro-phenyl)-propyl]-amide;

3-Methanesulfonylamino-2-phenyl-quinoline-4-carboxylic acid [cyclopropyl-(3-fluoro-phenyl)-methyl]-amide;

2-(3-Fluoro-phenyl)-3-methanesulfonylamino-quinoline-4-carboxylic acid (1-phenyl-propyl)-amide;

2-(3-Fluoro-phenyl)-3-methanesulfonylamino-quinoline-4-carboxylic acid (cyclopropyl-phenyl-methyl)-amide;

2-(3-Fluoro-phenyl)-3-methanesulfonylamino-quinoline-4-carboxylic acid [1-(3-fluoro-phenyl)-propyl]-amide;

2-(3-Fluoro-phenyl)-3-methanesulfonylamino-quinoline-4-carboxylic acid [cyclopropyl-(3-fluoro-phenyl)-methyl]-amide;

3-Methanesulfonylamino-2-phenyl-quinoline-4-carboxylic acid ((S)-1-phenyl-propyl)-amide;

3-Ethanesulfonylamino-2-phenyl-quinoline-4-carboxylic acid ((S)-1-phenyl-propyl)-amide;

2-Phenyl-3-trifluoromethanesulfonylamino-quinoline-4-carboxylic acid ((S)-1-phenyl-propyl)-amide;

2-Phenyl-3-(2,2,2-trifluoro-ethanesulfonylamino)-quinoline-4-carboxylic acid ((S)-1-phenyl-propyl)-amide;

2-Phenyl-3-(propane-1-sulfonylamino)-quinoline-4-carboxylic acid ((S)-1-phenyl-propyl)-amide;

2-Phenyl-3-(3,3,3-trifluoro-propane-1-sulfonylamino)-quinoline-4-carboxylic acid ((S)-1-phenyl-propyl)-amide;

3-Cyclopropanesulfonylamino-2-phenyl-quinoline-4-carboxylic acid ((S)-1-phenyl-propyl)-amide;

3-Methanesulfonylamino-2-phenyl-quinoline-4-carboxylic acid ((S)-cyclopropyl-phenyl-methyl)-amide;
3-Methanesulfonylamino-2-phenyl-quinoline-4-carboxylic acid [(S)-1-(3-fluoro-phenyl)-propyl]-amide;
3-Methanesulfonylamino-2-phenyl-quinoline-4-carboxylic acid [(S)-cyclopropyl-(3-fluoro-phenyl)-methyl]-amide;
2-(3-Fluoro-phenyl)-3-methanesulfonylamino-quinoline-4-carboxylic acid ((S)-1-phenyl-propyl)-amide;
2-(3-Fluoro-phenyl)-3-methanesulfonylamino-quinoline-4-carboxylic acid ((S)-cyclopropyl-phenyl-methyl)-amide;
2-(3-Fluoro-phenyl)-3-methanesulfonylamino-quinoline-4-carboxylic acid [(S)-1-(3-fluoro-phenyl)-propyl]-amide;
2-(3-Fluoro-phenyl)-3-methanesulfonylamino-quinoline-4-carboxylic acid [(S)-cyclopropyl-(3-fluoro-phenyl)-methyl]-amide;
3-(Methanesulfonylamino-methyl)-2-phenyl-quinoline-4-carboxylic acid (1-phenyl-propyl)-amide;
3-(Ethanesulfonylamino-methyl)-2-phenyl-quinoline-4-carboxylic acid (1-phenyl-propyl)-amide;
3-(Methanesulfonylamino-methyl)-2-phenyl-quinoline-4-carboxylic acid ((S)-1-phenyl-propyl)-amide,
3-(Ethanesulfonylamino-methyl)-2-phenyl-quinoline-4-carboxylic acid ((S)-1-phenyl-propyl)-amide,
N-[(1S)-cyclopropyl(phenyl)methyl]-3-[(methylsulfonyl)amino]-2-phenylquinolin-4-carboxamide,
N-[(1S)-cyclopropyl(3-fluorophenyl)methyl]-3-[(methylsulfonyl)amino]-2-phenylquinolin-4-carboxamide,
N-[(1S)-1-cyclohexylethyl]-3-[(methylsulfonyl)amino]-2-phenylquinolin-4-carboxamide
N-[(1R,2S)-2-hydroxy-1-phenylpropyl]-3-[(methylsulfonyl)amino]-2-phenylquinolin-4-carboxamide,
N—[(S)-Cyclopropyl(phenyl)methyl]-3-[(cyclopropylsulfonyl)amino]-2-phenylquinoline-4-carboxamide, and
3-(Methanesulfonyl-methyl-amino)-2-phenyl-quinoline-4-carboxylic acid ((S)-1-phenyl-propyl)-amide,
stereoisomers, enantiomers, in vivo-hydrolysable precursors and pharmaceutically acceptable salts thereof.

Compounds of the present invention have the advantage that they may be more soluble, be more easily absorbed and more efficacious in vivo, produce fewer side effects, be less toxic, be more potent, more selective, be longer acting, be less metabolized and/or have a better pharmacokinetic profile than, or have other useful pharmacological or physicochemical properties over known compounds. Using assays for functional activity described herein, compounds of the invention will be found to have $IC_{50}$'s of less than about 1 µM for NK-3 receptors and many compounds will be found to have $IC_{50}$'s of less than about 100 nM for NK-3 receptors.

ABBREVIATIONS AND DEFINITIONS

As used herein, unless otherwise indicated, $C_{1-6}$alkyl includes but is not limited to methyl, ethyl, n-propyl, n-butyl, i-propyl, i-butyl, t-butyl, s-butyl moieties, whether alone or part of another group and alkyl groups may be straight-chained or branched.

As used herein, unless otherwise indicated, $C_{1-6}$alkoxy includes but is not limited to —O-methyl, —O-ethyl, —O-n-propyl, —O-n-butyl, —O-i-propyl, —O-i-butyl, —O-t-butyl, —O-s-butyl moieties, whether alone or part of another group and alkoxy groups may be straight-chained or branched.

As used herein $C_{3-6}$cycloalkyl groups include but are not limited to the cyclic alkyl moieties cyclopropyl, cyclobutyl, cyclopentyl and cyclohexyl.

As used herein, unless otherwise indicated, $C_{2-6}$alkenyl includes but is not limited to 1-propenyl, 2-propenyl, 1-butenyl, 2-butenyl and 3-butenyl.

As used herein, unless otherwise indicated, $C_{2-6}$alkynyl includes but is not limited to ethynyl, 1-propynyl, 2-propynyl, 1-butynyl, 2-butynyl and 3-butynyl.

As used herein, unless otherwise indicated, halo or halogen refers to fluorine, chlorine, bromine, or iodine;

As used herein, aryl includes to phenyl and naphthyl;

As used herein, aromatic or non-aromatic heterocyclic rings include but are not limited to N- or C-linked furyl, imidazolyl, oxazolyl, pyrrolidinyl, thiazolyl, thiophenyl, pyrrolyl, morpholinyl, piperidinyl, piperazinyl, pyrazinyl, pyridyl, pyrimidinyl, indanyl, indolyl, quinolinyl, isoquinolinyl, quinazolinyl, quinoxalinyl, benzo[b]thiophenyl, benzoxazolyl, or benzthiazolyl;

DCM refers to dichloromethane;

EtOAc refers to ethyl acetate;

EDC refers to 1-(3-dimethylaminopropyl)-3-ethylcarbodiimide;

EDTA refers to ethylenediaminetetraacetic acid;

HEPES refers to 4-(2-hydroxyethyl)-1-piperazine ethane sulfonic acid, monosodium salt, and TEA refers to triethylamine.

In processes described herein, where necessary, hydroxy, amino, or other reactive groups may be protected using a protecting group as described in the standard text "Protecting groups in Organic Synthesis", $3^{rd}$ Edition (1999) by Greene and Wuts.

Unless otherwise stated, reactions are conducted under an inert atmosphere, preferably under a nitrogen atmosphere and are usually conducted at a pressure of about one to about three atmospheres, preferably at ambient pressure (about one atmosphere).

The compounds of the invention and intermediates may be isolated from their reaction mixtures by standard techniques.

Acid addition salts of the compounds of Formula I which may be mentioned include salts of mineral acids, for example the hydrochloride and hydrobromide salts; and salts formed with organic acids such as formate, acetate, maleate, benzoate, tartrate, and fumarate salts.

Acid addition salts of compounds of Formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

Certain compounds of Formula I may exist in tautomeric or enantiomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions that will not cause racemization.

Synthesis and Schemes
Compounds of Formula I may be made by the methods illustrated in the following schemes.
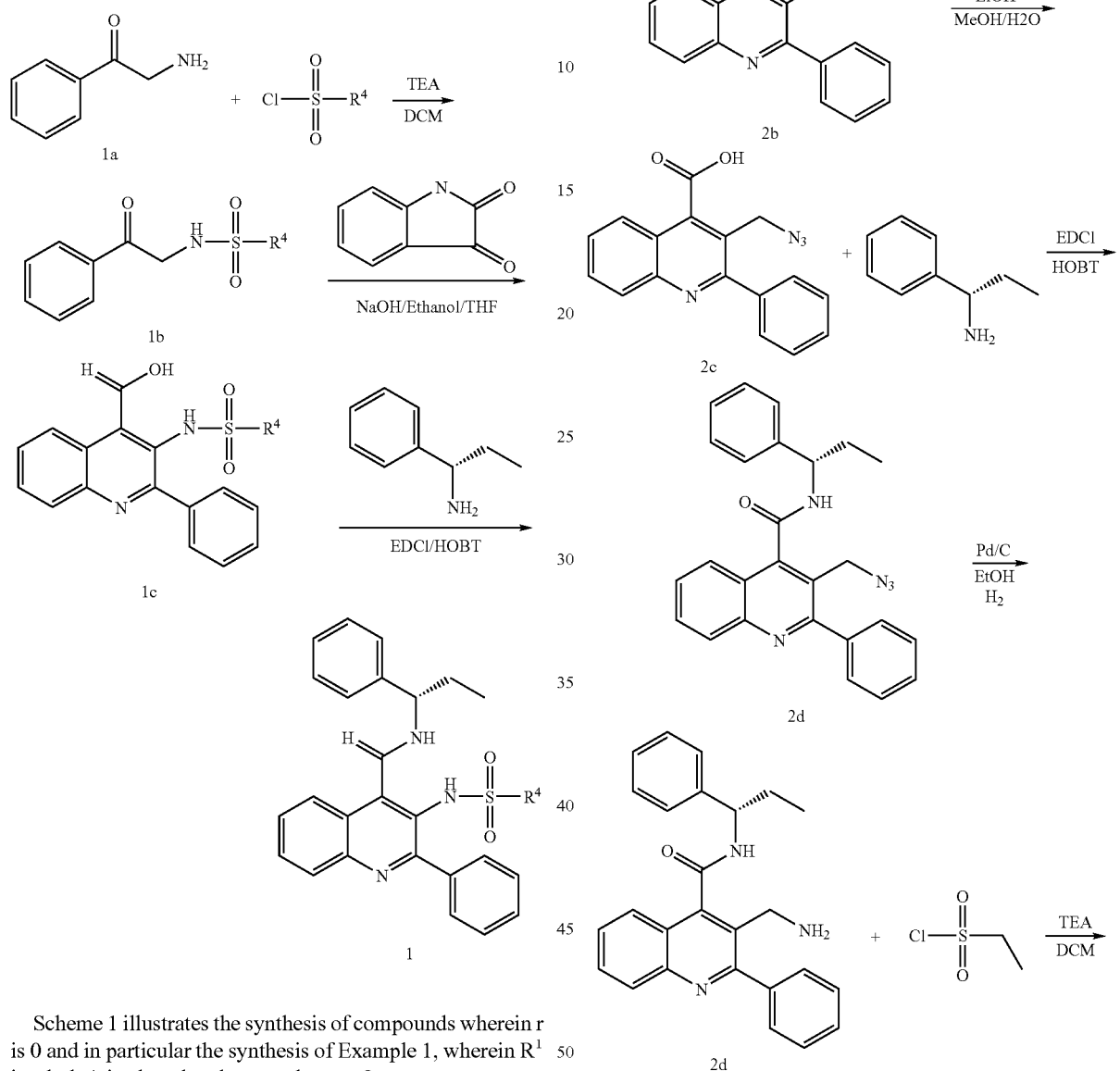
Scheme 1 illustrates the synthesis of compounds wherein r is 0 and in particular the synthesis of Example 1, wherein $R^1$ is ethyl, A is phenyl and n, q and m are 0.
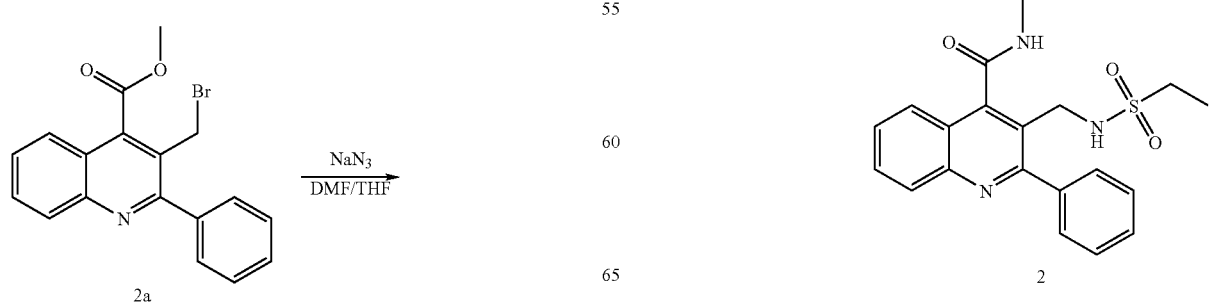

Scheme 2 illustrates the synthesis of compounds wherein r is greater than 0 and in particular the synthesis of Example 3.

Generally, compounds of the invention may be made by reacting 2-amino-1-phenyl-ethanone and an alkyl sulfonyl chloride in the presence of TEA and DCM to form an N-(2-oxo-2-phenyl-ethyl)-alkylsulfonamide; treating the alkylsulfonamide with NaOH, and THF in ethanol to form a 3-alkyl-sulfonylamino-2-phenyl-quinoline-4-carboxylic acid, and reacting the carboxylic acid with an arylamine in the presence of EDCI and HOBT to form a compound of Formula I.

Other compounds of the invention may be made by treating a bromoalkyl-2-phenyl-quinoline-4-carboxylic acid methyl ester with $NaN_3$ in DMF/THF to form an azido derivative thereof; treating the derivative with LiOH in ethanol/water to form an azidocarboxylic acid; reacting the acid with an arylamine in the presence of EDCI and HOBT to form an azido quinoline; treating the azido quinoline with palladium on carbon in ethanol to form an amine, and reacting the amine and an alkyl sulfonyl chloride in the presence of TEA and DCM to form a compound of Formula I.

In a further aspect the invention relates to compounds described herein wherein one or more of the atoms is a radioisotope of the same element. In a particular form of this aspect of the invention the compound is labeled with tritium. Such radio-labeled compounds are synthesized either by incorporating radio-labeled starting materials or, in the case of tritium, exchange of hydrogen for tritium by known methods. Known methods include (1) electrophilic halogenation, followed by reduction of the halogen in the presence of a tritium source, for example, by hydrogenation with tritium gas in the presence of a palladium catalyst, or (2) exchange of hydrogen for tritium performed in the presence of tritium gas and a suitable organometallic (e.g. palladium) catalyst.

Compounds of the invention labeled with tritium are useful for the discovery of novel medicinal compounds that bind to and modulate the activity, by agonism, partial agonism, or antagonism, of an NK-3 receptor. Such tritium-labeled compounds may be used in assays that measure the displacement of such compounds to assess the binding of ligands that bind to NK-3 receptors.

In a further aspect the invention relates to compounds described herein additionally comprising one or more atoms of a radioisotope. In a particular form of this aspect of the invention the compound comprises a radioactive halogen. Such radio-labeled compounds are synthesized by incorporating radio-labeled starting materials by known methods. Particular embodiments of this aspect of the invention are those in which the radioisotope is selected from $^{18}F$, $^{123}I$, $^{125}I$, $^{131}I$, $^{75}Br$, $^{76}Br$, $^{77}Br$ or $^{82}Br$. A most particular embodiment of this aspect of the invention is that in which the radioisotope is $^{18}F$. Such compounds comprising one or more atoms of a radioisotope are useful as positron emission tomography (PET) ligands and for other uses and techniques to determine the location of NK3 receptors.

Therapeutic Uses of Compounds:

In another aspect the invention relates to compounds in accord with Formula I described herein and the use of such compounds in therapy and in compositions useful for therapy.

In another aspect the invention encompasses the use of compounds described herein for the therapy of diseases mediated through the action of NK-3 receptors. Such an aspect encompasses methods of treatment or prophylaxis of diseases or conditions in which modulation of the NK-3 receptor is beneficial which methods comprise administering a therapeutically effective amount of an antagonistic compound of the invention to a subject suffering from said disease or condition.

One embodiment of this aspect of the invention is a method of treatment or prophylaxis of disorders, wherein the disorder is depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, or testicular cancer comprising administering a pharmacologically effective amount of a compound of Formula I to a patient in need thereof.

A further aspect of the invention is the use of a compound according to the invention, an enantiomer thereof or a pharmaceutically acceptable salt thereof, in the treatment or prophylaxis of a disease or condition in which modulation of the NK-3 receptor is beneficial. Particular diseases and conditions that may be treated are depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer. More particular embodiments encompass uses of a compound in the treatment or prophylaxis of anxiety, depression, schizophrenia and obesity.

A further aspect of the invention is the use of a compound according to the invention, an enantiomer thereof or a pharmaceutically acceptable salt thereof, in the manufacture of a medicament for the treatment or prophylaxis of the diseases or conditions mentioned herein. A particular embodiment of this aspect of the invention is the use of a compound of the invention in the manufacture of a medicament for treatment or prophylaxis of depression, anxiety, schizophrenia, cognitive disorders, psychoses, obesity, inflammatory diseases including irritable bowel syndrome and inflammatory bowel disorder, emesis, pre-eclampsia, chronic obstructive pulmonary disease, disorders associated with excessive gonadotrophins and/or androgens including dysmenorrhea, benign prostatic hyperplasia, prostatic cancer, and testicular cancer.

Pharmaceutical Compositions

Compounds of the invention, enantiomers thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent, lubricant or carrier.

Examples of diluents, lubricants and carriers are
  for tablets and dragees: lactose, starch, talc, stearic acid;
  for capsules: tartaric acid or lactose;
  for injectable solutions: water, alcohols, glycerin, vegetable oils;
  for suppositories: natural or hardened oils or waxes.

There is also provided a process for the preparation of such a pharmaceutical composition which process comprises mixing or compounding the ingredients together and forming the mixed ingredients into tablets or suppositories, encapsulating the ingredients in capsules or dissolving the ingredients to form injectable solutions.

Pharmaceutically acceptable derivatives include solvates and salts. For example, the compounds of the invention may form acid addition salts with acids, such as conventional pharmaceutically acceptable acids including maleic, hydrochloric, hydrobromic, phosphoric, acetic, fumaric, salicylic, citric, lactic, mandelic, tartaric and methanesulfonic acids.

Acid addition salts of the compounds of Formula I which may be mentioned include salts of mineral acids, for example the hydrochloride and hydrobromide salts; and salts formed with organic acids such as formate, acetate, maleate, benzoate, tartrate, and fumarate salts. Acid addition salts of compounds of Formula I may be formed by reacting the free base or a salt, enantiomer or protected derivative thereof, with one or more equivalents of the appropriate acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

For the uses, methods, medicaments and compositions mentioned herein the amount of compound used and the dosage administered will, of course, vary with the compound employed, the mode of administration and the treatment desired. However, in general, satisfactory results are obtained when the compounds of the invention are administered at a daily dosage of about 0.1 mg to about 20 mg/kg of animal body weight. Such doses may be given in divided doses 1 to 4 times a day or in sustained release form. For man, the total daily dose is in the range of from 5 mg to 1,400 mg, more preferably from 10 mg to 100 mg, and unit dosage forms suitable for oral administration comprise from 2 mg to 1,400 mg of the compound admixed with a solid or liquid pharmaceutical carriers, lubricants and diluents.

Some compounds of the invention may exist in tautomeric, enantiomeric, stereoisomeric or geometric isomeric forms, all of which are included within the scope of the invention. The various optical isomers may be isolated by separation of a racemic mixture of the compounds using conventional techniques, e.g. fractional crystallization, or chiral HPLC. Alternatively the individual enantiomers may be made by reaction of the appropriate optically active starting materials under reaction conditions that will not cause racemization.

Exemplary compounds of the invention may be prepared by processes analogous to that described in Scheme 1. Those of skill in the art will readily appreciate that many suitable amines and acid chlorides and carboxylic acids may be used to form compounds within the scope of the subject matter described herein as Formula I.

EXEMPLARY COMPOUNDS

The exemplary compounds and processes describe the invention by way of illustration and example for clarity of understanding. However to those skilled in the art, upon contemplation of the teaching of compounds, processes and methods of this invention, modifications and changes will be apparent that may be made thereto without departing from the spirit or scope of the invention.

Example 1

3-[(Methylsulfonyl)amino]-2-phenyl-N-[(1S)-1-phenylpropyl]quinolin-4-carboxamide (1) (Identifiers in Example 1 Refer to Scheme 1)

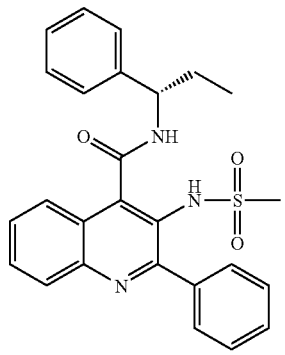

A solution of 3-[(methylsulfonyl)amino]-2-phenylquinoline-4-carboxylic acid (1c) (342 mg, 1.0 mmol), HOBT hydrate (231 mg, 1.5 mmol), 4-methylmorpholine (276 μL, 1.5 mmol) in tetrahydrofuran (50 ml) was added EDCI (289 mg, 1.5 mmol) at RT under $N_2$. (S)-1-Phenyl propylamine (135 mg, 1.0 mmol) was then added and the reaction mixture stirred at RT for 12 h. All solvent was removed in vacuo and the residue was partitioned between ethyl acetate and 10% aqueous sodium bicarbonate solution, dried over sodium sulfate and then concentrated in vacuo. The residue was purified by chromatography eluting with 15-25% ethyl acetate/hexane to give the title compound (70 mg, 15%) as a solid. $^1$H NMR (300 MHz, $CDCl_3$) δ 0.94 (t, 3H), 1.97 (m, 2H), 3.44 (s, 3H), 5.17 (q, 1H), 5.47 (m, 2H), 7.32 (d, 2H), 7.34 (d, 2H), 7.39 (m, 1H), 7.78 (m, 2H), 7.84 (m, 2H), 8.08 (m, 1H), 8.30 (m, 2H), 8.42 (m, 2H). MS APCI, m/z=460 (M+1). LCMS: 2.51 min.

The starting acid, 3-[(methylsulfonyl)amino]-2-phenylquinoline-4-carboxylic acid (1c), was prepared in the following manner:

N-(2-oxo-2-phenylethyl)methanesulfonamide (1b)

To a solution of 2-amino-1-phenylethanonehydrochloride (1a) (1715 mg, 10 mmol) in DMF (20 mL) was added TEA (2.8 mL, 20 mmol). Upon cooling under ice-water bath, methylsulfonyl chloride (0.77 mL, 10 mmol) was added slowly and the reaction mixture stirred at RT for 12 h. The mixture was partitioned between dichloromethane and brine, dried over sodium sulfate and then concentrated in vacuo to give the title compound (2100 mg, 98%) as an off white solid. MS APCI, m/z=214 (M+1). LCMS: 1.19 min.

3-[(methylsulfonyl)amino]-2-phenylquinoline-4-carboxylic acid (1c)

To isatin (441 mg, 3 mmol) was added a solution of sodium hydroxide (1.15 g, 29.0 mmol) in water (2.5 mL). The resulting brown precipitate was stirred vigorously at RT for 20 minutes before being heated to 85° C. A solution of N-(2-oxo-2-phenylethyl)methanesulfonamide (1b) (639 mg, 3.0 mmol) in ethanol/THF/water (6.3 mL/1.25 mL/6.3 mL was then added dropwise over 30 minutes. The reaction mixture was stirred at 85° C. for further 4 h before cooling to RT. All organic solvents were removed in vacuo and the aqueous residue reduced to a volume of approximately 6 mL. The aqueous residue was washed with ether (3×10 mL) and then the aqueous residue were acidified with cooling to pH 4 with acetic acid. The precipitate formed were collected, washed with water and dried to give the title compound as a solid (721 mg, 70.3%). $^1$H NMR (300 MHz, CDCl$_3$) δ 3.11 (s, 3H), 7.05 (d, 1H), 7.39 (d, 2H), 7.64 (m, 2H), 7.78 (m, 1H), 8.06 (m, 1H), 8.19 (m, 1H), 8.47 (m, 1H), 10.03 (b, 2H). MS APCI, m/z=343 (M+1). LCMS: 1.07 min.

Example 2

3-(Methylsulfonylamino-methyl)-2-phenyl-quinoline-4-carboxylic acid ((S)-1-phenyl-propyl)-amide (Identifiers in Examples 2 and 3 Refer to Scheme 2)

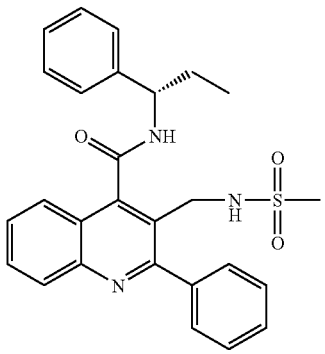

A solution of 3-(aminomethyl)-2-phenyl-N-[(1S)-1-phenylpropyl]quinoline-4-carboxamide (2e) (197 mg, 0.5 mmol) in DCM (30 ml) was added triethylamine (140 μL, 1.0 mmol) under N$_2$. Upon cooling with ice-water bath, methanesulfonyl chloride (39 μL, 0.51 mmol) was added dropwise and the reaction mixture stirred at RT for additional 2 h. Washed the mixture with brine (10 mL) and the organic phase was separated and dried over sodium sulfate and then concentrated in vacuo. The residue was purified by chromatography eluting with 15-25% ethyl acetate/hexane to give the title compound (79 mg, 42%) as a solid. $^1$H NMR (300 MHz, CDCl$_3$) δ 0.94 (t, 3H), 1.95 (m, 2H), 2.99 (s, 3H), 4.88 (s, 2H), 5.25 (q, 1H), 6.66 (b, 2H), 7.30 (d, 2H), 7.34 (d, 2H), 7.39 (m, 1H), 7.78 (m, 2H), 7.84 (m, 2H), 8.08 (m, 1H), 8.30 (m, 2H), 8.20 (m, 2H). MS APCI, m/z=474 (M+1). LCMS: 2.16 min.

Example 3

3-{[(Ethylsulfonyl)amino]methyl}-2-phenyl-N-[(1S)-1-phenylpropyl]quinoline-4-carboxamide

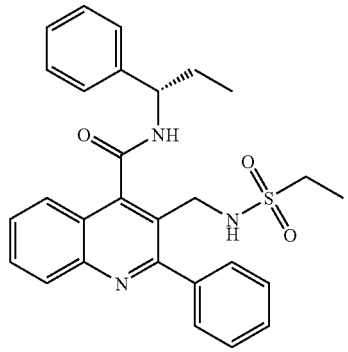

Using a procedure similar to that described in Example 2, but using ethanesulfonyl chloride (48.6 μL, 0.51 mmol) as a component provided the title compound as a white solid. (90 mg, 38%). $^1$H NMR (300 MHz, CDCl$_3$) δ 0.92 (t, 3H), 1.32 (t, 3H), 1.95 (m, 2H), 3.04 (q, 2H), 4.87 (s, 2H), 5.17 (q, 1H), 5.48 (b, 2H), 7.25 (d, 2H), 7.34 (d, 2H), 7.39 (m, 1H), 7.78 (m, 2H), 7.84 (m, 2H), 8.08 (m, 1H), 8.30 (m, 2H), 8.17 (m, 2H). MS APCI, m/z=488 (M+1). LCMS: 2.24 min.

The starting amine, 3-(aminomethyl)-2-phenyl-N-[(1S)-1-phenylpropyl]quinoline-4-carboxamide for Examples 2 and 3 was prepared in the following manner:

Methyl 3-(azidomethyl)-2-phenylquinoline-4-carboxylate (2b)

To a solution of 3-(bromomethyl)-2-phenylquinoline-4-carboxylate (2a) (2000 mg, 5.618 mmol) in THF/DMF (50 mL/10 mL) was added sodium azide (402 mg, 6.18 mmol) and the reaction mixture stirred at RT under N$_2$ for 12 h. All solvent was removed in vacuo and the residue was partitioned between ethyl acetate and brine, dried over sodium sulfate and then concentrated in vacuo. The residue was purified by chromatography eluting with 10% ethyl acetate/hexane to give the title compound (1781 mg, 99.7%) as an off white solid. MS APCI, m/z=319 (M+1). LCMS: 2.34 min.

3-(azidomethyl)-2-phenylquinoline-4-carboxylic acid (2c)

To a solution of methyl 3-(azidomethyl)-2-phenylquinoline-4-carboxylate (2b) (1781 mg, 5.0 mmol) in methanol (50 mL) was added the solution of lithium hydroxide monohydrate (674 mg, 28.1 mmol) in 25 mL water. The reaction mixture was stirred at reflux for 4 h and the residue was acidified with 1N HCl to pH 2. The volume of reaction mixture was reduced under reduced pressure. The resulting aqueous phase was extracted with ethyl acetate (150 mL). The organic phase was separated and washed with brine (20 ml) and dried over sodium sulfate and then concentrated in vacuo. Crystallization from ethyl acetate/hexane to afford the title compound (1200 mg, 66%) as an off white solid. MS APCI, m/z=305 (M+1). LCMS: 1.09 min.

3-(azidomethyl)-2-phenyl-N-[(1s)-1-phenylpropyl]quinoline-4-carboxamide (2d)

A solution of 3-(azidomethy)-2-phenylquinoline-4-carboxylic acid (2c) (997 mg, 3.28 mmol), HOBT hydrate (760 mg, 4.92 mmol), 4-methylmorpholine (551 μL, 4.92 mmol) in tetrahydrofuran (50 mL) was added EDC (960 mg, 4.92 mmol) at RT under N$_2$. (S)-1-Phenyl propylamine (488.5 mg, 3.62 mmol) was then added and the reaction mixture stirred at RT for 12 h. All solvent was removed in vacuo and the residue was partitioned between ethyl acetate and 10% aqueous sodium bicarbonate solution, dried over sodium sulfate and then concentrated in vacuo. The residue was purified by chromatography eluting with 15-25% ethyl acetate/hexane to give the title compound (1000 mg, 73%) as a light-yellow solid. $^1$H NMR (300 MHz, CDCl$_3$) δ 0.94 (t, 3H), 2.01 (m, 2H), 5.17 (q, 1H), 5.19 (s, 2H), 5.72 (b, 1H), 7.21 (d, 2H), 7.34 (d, 2H), 7.39 (m, 1H), 7.78 (m, 2H), 7.84 (m, 2H), 8.08 (m, 1H), 8.30 (m, 2H), 8.49 (m, 2H). MS APCI, m/z=422 (M+1). LCMS: 2.47 min.

3-(aminomethyl)-2-phenyl-N-[(1s)-1-phenylpropyl] quinoline-4-carboxamide (2e)

A solution of 3-(azidomethyl)-2-phenyl-N-[(1s)-1-phenylpropyl]quinoline-4-carboxamide (2d) (1000 mg, 2.37 mmol) in ethanol (200 mL) were added Pd/C (10%, 1190 mg) and HCl (2N, 2.5 mL) was added. The reaction mixture were hydrogenated under 50 psi $H_2$ at RT for 1.5 h. The catalyst was removed by filtration through a thick layer of diatomaceous earth, the filter was washed with ethanol and the washes and the ethanol solvent was combined and concentrated in vacuo. Crystallization from dichloromethane and ether afforded the title compound (940 mg, 92%) as a hydrogen chloride salt. $^1$H NMR (300 MHz, $CDCl_3$) δ 0.92 (t, 3H), 2.01 (m, 2H), 3.18 (b, 3H), 4.39 (t, 2H), 5.16 (q, 1H), 7.30 (d, 2H), 7.34 (d, 2H), 7.39 (m, 1H), 7.78 (m, 2H), 7.84 (m, 2H), 8.08 (m, 1H), 8.30 (m, 2H), 8.44 (m, 2H). MS APCI, m/z=396 (M+1). LCMS: 1.70 min.

Example 4

3-[Methyl(methylsulfonyl)amino]-2-phenyl-N-[(1S)-1-phenylpropyl]quinolin-4-carboxamide

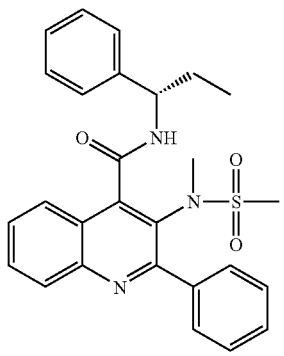

A solution of 3-[(methylsulfonyl)amino]-2-phenyl-N-[(1S)-1-phenylpropyl]quinolin-4-carboxamide (1) (459 mg, 1.0 mmol) in 5 ml DMF was added $Cs_2CO_3$ (325.8 mg, 1.0 mmol) and $CH_3I$ (62.3 μL, 1.0 mmol). The reaction mixture was stirred at RT under $N_2$ for 2 h. All solvent was removed in vacuo and the residue was partitioned between ethyl acetate and 10% aqueous sodium bicarbonate solution, dried over sodium sulfate and then concentrated in vacuo. The residue was purified by recrystallization from ether/$CH_2Cl_2$ to give the title compound (210 mg, 44.4%) as a solid. $^1$H NMR (300 MHz, $CDCl_3$) δ 0.94 (t, 3H), 1.97 (m, 2H), 2.71 (s, 3H), 3.43 (s, 3H), 5.10 (q, 1H), 5.14 (b, 1H), 7.32 (d, 2H), 7.34 (d, 2H), 7.39 (m, 1H), 7.78 (m, 2H), 7.84 (m, 2H), 8.08 (m, 1H), 8.30 (m, 2H), 8.42 (m, 2H). MS APCI, m/z=474 (M+1). LCMS: 2.32 min.

Example 5

N-[(1S)-cyclopropyl(phenyl)methyl]-3-[(methylsulfonyl)amino]-2-phenylquinolin-4-carboxamide (3)

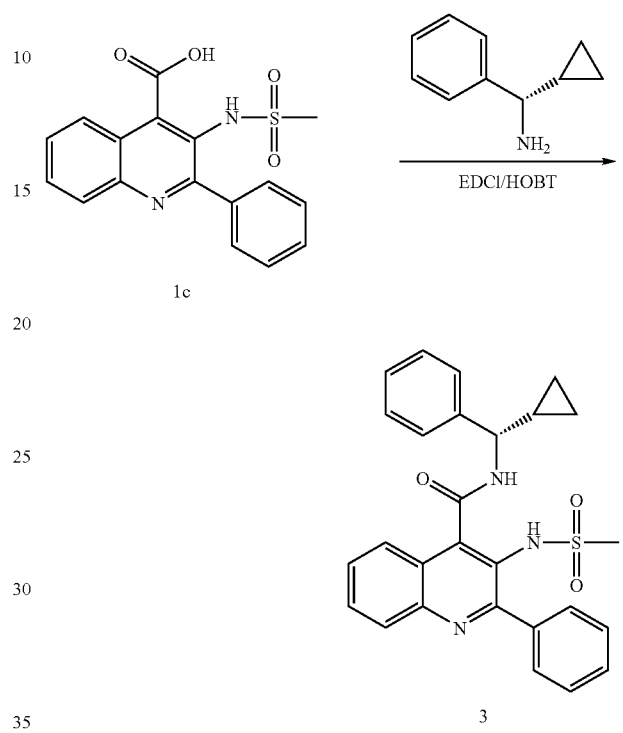

Using a procedure similar to that described in Example 1, except using (S)-1-cyclopropyl-1-phenylmethanamine as amine component, the title compound (3) was obtained (50%) as a white solid. $^1$H NMR (300 MHz, $CDCl_3$) δ 0.44 (m, 2H), 0.61 (m, 2H), 1.57 (m, 1H), 3.06 (s, 3H), 4.76 (q, 1H), 7.32 (d, 2H), 7.34 (d, 2H), 7.39 (m, 1H), 7.78 (m, 2H), 7.84 (m, 2H), 8.08 (m, 1H), 8.30 (m, 2H), 8.42 (m, 2H). MS APCI, m/z=472 (M+1). LCMS: 2.21 min.

Example 6

N-[(1S)-cyclopropyl(3-fluorophenyl)methyl]-3-[(methylsulfonyl)amino]-2-phenylquinolin-4-carboxamide (4)

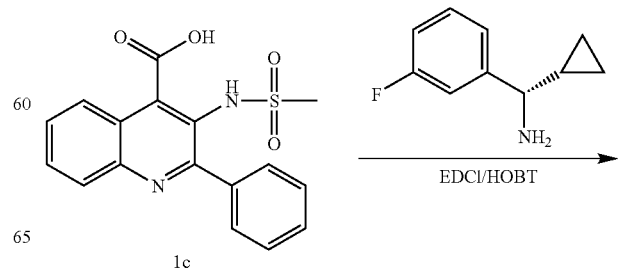

-continued

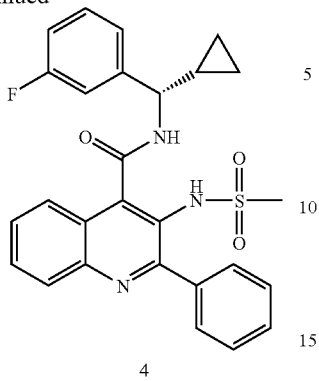

4

Using a procedure similar to that described in Example 1, except using (S)-1-cyclopropyl-1-(3-fluorophenyl)methanamine as amine component, the title compound (4) was obtained (35%) as a white solid. $^1$H NMR (300 MHz, CDCl$_3$) δ 0.46 (m, 2H), 0.66 (m, 2H), 1.57 (m, 1H), 3.07 (s, 3H), 4.99 (q, 1H), 7.32 (d, 2H), 7.34 (m, H), 7.39 (m, 1H), 7.78 (m, 2H), 7.84 (m, 2H), 8.08 (m, 1H), 8.30 (m, 2H), 8.42 (m, 2H). MS APCI, m/z=490 (M+1). LCMS: 2.24 min.

Example 7

N-[(1S)-1-cyclohexylethyl]-3-[(methylsulfonyl) amino]-2-phenylquinolin-4-carboxamide (5)

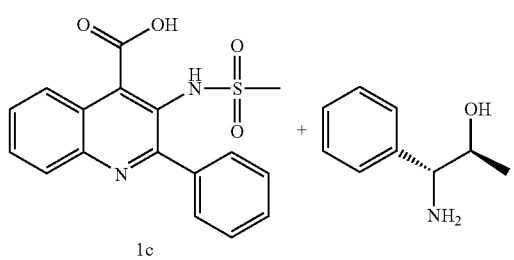

Using a procedure similar to that described in Example 1, except using (1S)-1-cyclohexylethanamine as amine component, the title compound (5) was obtained (36%) as a white solid. $^1$H NMR (300 MHz, CDCl$_3$) δ 1.12-1.16 (m, 4H), 1.26 (d, 2H), 1.45-1.55 (m, 4H), 1.57 (m, 2H), 1.92 (m, 1H), 2.3 (s, 3H), 4.23 (q, 1H), 6.62 (d, 1H), 7.37 (d, 2H), 7.56 (m, 2H), 7.64 (m, 2H), 7.78 (m, 1H), 7.80 (d, 1H), 8.14 (d, 1H). MS APCI, m/z=452 (M+1). LCMS: 2.30 min.

Example 8

N-[(1R,2S)-2-hydroxy-1-phenylpropyl]-3-[(methylsulfonyl)amino]-2-phenylquinolin-4-carboxamide (6)

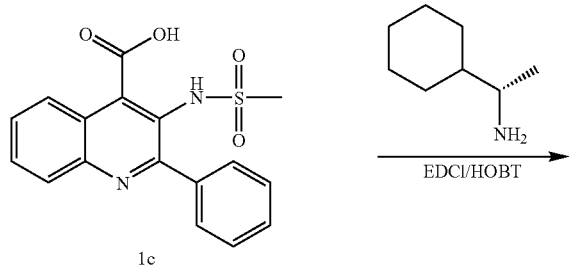

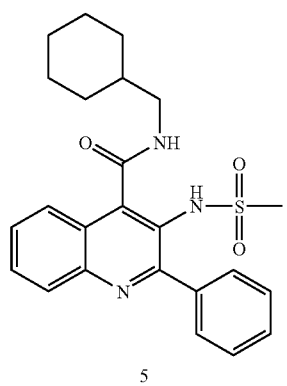

6

A solution of 3-methanesulfonylamino-2-phenyl-4-carboxylic acid (1c) (250 mg, 0.73 mmol), HOBt hydrate (148 mg, 1.1 mmol), 4-methylmorpholine (160 μL, 1.46 mmol) in methylene chloride (15 mL) was added EDCI (210 mg, 1.1 mmol) at RT under N$_2$. A mixture of (1R,2S)-1-amino-1-phenylpropan-2-ol hydrochloride and 4-methylmorpholine (193 μL, 1.75 mmol), in methylene chloride (5 mL) was added and the reaction mixture was stirred at RT for 16 h. Solution is partitioned against water and twice extracted with methylene chloride. The combined organic extracts are washed with brine, dried over magnesium sulfate and then concentrated in vacuo with added silica. The compound is subsequently eluted off the silica and chromatographed, eluting with 15-30% ethyl acetate/dichloromethane to give the title compound (167 mg, 48%). $^1$H NMR (500.333 MHz, CDCl3) δ 1.10 (d, J=6.6 Hz, 3H), 2.23 (s, 3H), 2.69 (d', J=6.7 Hz, 1H), 4.44-4.47 (m, 1H), 5.35 (dd, J=8.4, 3.3 Hz, 1H), 7.35 (d, J=7.2 Hz, 1H), 7.39 (dd, J=6.9, 6.9 Hz, 2H), 7.44 (d, J=7.5 Hz, 2H), 7.47-7.55 (m, 4H), 7.71-7.78 (m, 4H), 8.16 (d, J=8.4 Hz, 1H) MS APCI, m/z=476.1 (M+1). LCMS: 1.86 min.

The starting amine, (1R,2S)-1-amino-1-phenylpropan-2-ol hydrochloride, was prepared from (1S,2S)-(–)-1-phenylpropylene oxide by known methods.

Example 9

3-[(Cyclopropylsulfonyl)amino]-2-phenyl-N-[(1S)-1-phenylpropyl]quinoline-4-carboxamide (7)

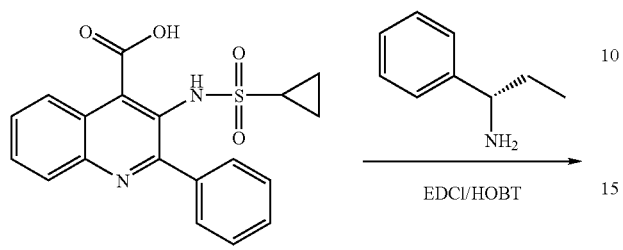

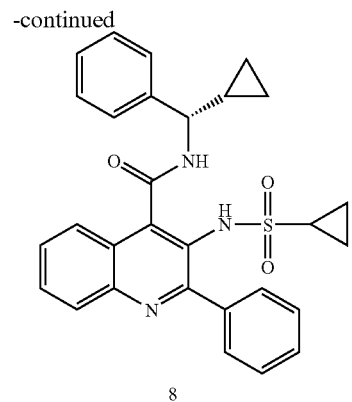

Using a procedure similar to that described in Example 1, except using 3-[(cyclopropylsulfonyl)amino]-2-phenylquinoline-4-carboxylic acid as the acid component, the title compound (7) was obtained (85%) as a white solid. $^1$H NMR (300 MHz, CDCl$_3$) δ 0.79-0.82 (m, 2H), 0.95 (t, 3H), 1.09-1.11 (m, 2H), 1.87-2.07 (m, 2H), 4.13 (m, 1H), 5.19 (q, 1H), 7.06 (d, 1H), 7.09 (d, 2H), 7.32 (m, 1H), 7.37 (d, 2H), 7.56 (m, 2H), 7.64 (m, 2H), 7.78 (m, 1H), 7.80 (d, 1H), 7.93 (m, 1H), 8.18 (d, 1H). MS APCI, m/z=486 (M+1). LCMS: 2.31 min.

Example 10

N—[(S)-Cyclopropyl(phenyl)methyl]-3-[(cyclopropylsulfonyl)amino]-2-phenylquinoline-4-carboxamide (8)

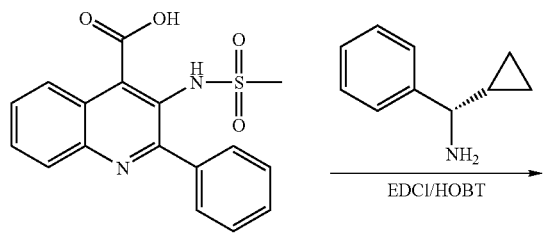

Using a procedure similar to that described in Example 1, except using 3-[(cyclopropylsulfonyl)amino]-2-phenylquinoline-4-carboxylic acid as the acid component, the title compound (8) was obtained (45%) as a white solid. $^1$H NMR (300 MHz, CDCl$_3$) δ 0.43 (m, 2H), 0.63 (m, 2H), 0.79-1.11 (m, 4H), 0.95 (t, 3H), 1.56 (m, 1H), 3.63 (m, 1H), 4.75 (q, 1H), 7.04 (d, 1H), 7.09 (d, 2H), 7.32 (m, 1H), 7.37 (d, 2H), 7.56 (m, 2H), 7.64 (m, 2H), 7.78 (m, 1H), 7.80 (d, 1H), 7.93 (m, 1H), 8.18 (d, 1H). MS APCI, m/z=498 (M+1). LCMS: 2.37 min.

Biological Tests

NK-3 Receptor Binding Activity:

Generally, NK-3r binding activity may be assessed using assays performed as described in Krause et al., (Proc. Natl. Acad. Sci. USA 94: 310-315, 1997). NK-3r complementary DNA is cloned from human hypothalamic RNA using standard procedures. The receptor cDNA is inserted into a suitable expression vector transfected into a Chinese hamster ovary cell line, and a stably expressing clonal cell line may be isolated, characterized and used for experiments.

Cells may be grown in tissue culture medium by techniques known to those of skill in the art and recovered by low speed centrifugation. Cell pellets may be homogenized, total cellular membranes isolated by high-speed centrifugation and suspended in buffered saline. Generally, receptor binding assays may be performed by incubating suitable amounts of purified membrane preparations with [$^{125}$I]-methylPhe7-neurokinin B, in the presence or absence of test compounds. Membrane proteins may be harvested by rapid filtration and radioactivity may be quantitated in a β-plate scintillation counter. Nonspecific binding may be distinguished from specific binding by use of suitable controls and the affinity of compounds for the expressed receptor may be determined by using different concentrations of compounds.

Preparation of Membranes from CHO Cells Transfected with Cloned NK-3 Receptors:

A human NK-3 receptor gene was cloned using methods similar to those described for other human NK receptors (Aharony et al., Mol. Pharmacol. 45:9-19, 1994; Caccese et al., Neuropeptides 33, 239-243, 1999). The DNA sequence of the cloned NK-3 receptor differed from the published sequence (Buell et al., FEBS Letts. 299, 90-95, 1992; Huang et al., Biochem. Biophys. Res. Commun. 184, 966-972, 1992) having a silent single T>C base change at nucleotide 1320 of the coding sequence. Since the change is silent, the cloned gene provides a primary amino acid sequence for the encoded NK-3 receptor protein identical to the published sequence. The receptor cDNA was used to transfect CHO-K1 cells using standard methods and a clone stably-expressing the receptor was isolated and characterized. Plasma membranes from these cells were prepared as published (Aharony et al., 1994).

Cells were harvested and centrifuged to remove medium. The pelleted cells were homogenized (Brinkman Polytron, three 15 sec bursts on ice) in a buffer consisting of 50 mM Tris-HCl (pH 7.4), 120 mM NaCl, 5 mM KCl, 10 mM EDTA and protease inhibitors (0.1 mg/ml soybean trypsin inhibitor, and 1 mM iodoacetamide). The homogenate was centrifuged at 1000×g for 10 min at 4° C. to remove cell debris. Pellets were washed once with homogenizing buffer. Supernatants were combined and centrifuged at 40,000×g for 20 min at 4° C. The membrane-containing pellet was homogenized with a Polytron as before. The suspension was centrifuged at 40,000×g for 20 min at 4° C., the pellet suspended in buffer (20 mM HEPES, pH 7.4 containing 3 mM $MgCl_2$, 30 mM KCl, and 100 µM thiorphan) and the protein concentration determined. The membrane suspension was then diluted to 3 mg/ml with buffer containing 0.02% BSA, and flash frozen. Samples were stored at −80° C. until used.

Assay for NK-3 Receptor Binding Activity:

A receptor binding assay method with [$^{125}$I]-MePhe7-NKB was modified from that described by Aharony et al., J. Pharmacol. Exper. Ther., 274:1216-1221, 1995.

Competition experiments were carried out in 0.2 mL assay buffer (50 mM Tris-HCl, 4 mM $MnCl_2$, 10 µM thiorphan, pH 7.4) containing membranes (2 µg protein/reaction), tested competitors, and [$^{125}$I]-MePhe7NKB (0.2 nM). Unlabeled homologue ligand (0.5 µM) was used to define nonspecific binding. Incubations were carried out at 25° C. for 90 min. Receptor-bound ligand was isolated by vacuum filtration in a Packard Harvester onto GF/C plates presoaked in 0.5% BSA. Plates were washed with 0.02 M Tris, pH 7.4. Computation of equilibrium binding constants ($K_D$ and $K_i$), receptor density (Bmax), and statistical analysis was carried out as published previously (Aharony et al., 1995) using GraphPad Prism or IDBS XLfit software.

NK-3 Functional Activity:

Generally, NK-3 functional activity may be assessed by using calcium mobilization assays in stable NK-3r-expressing cell lines. Calcium mobilization induced by the methylPhe7-neurokinin B agonist may be monitored using a FLIPR (Molecular Devices) instrument in the manner described by the manufacturer. Agonists may be added to the cells and fluorescence responses continuously recorded for up to 5 min. The actions of antagonists may be assessed by preincubating cells prior to administration of the methylPhe7-neurokinin B agonist. The action of agonists may be assessed by observing their intrinsic activity in such a system.

Assay for NK-3 Functional Activity:

NK-3 receptor expressing CHO cells were maintained in growth media (Ham's F12 medium, 10% FBS, 2 mM L-glutamine, and 50 mg/mL Hygromycin B). One day prior to the assay cells were dispensed into 384-well plates in Ultraculture media (Cambrex Bio Science) with 2 mM L-glutamine to achieve 70-90% confluency. To quantify NK-3 receptor-induced calcium mobilization, cells were first washed with assay buffer consisting of Hanks' Balanced Salt Solution, 15 mM HEPES, and 2.5 mM probenecid, pH 7.4. The cells were then loaded with Fluo4/AM dye (4.4 µM) in assay buffer. Cells were incubated for one hour and then washed with assay buffer, exposed to 0.02-300 nM senktide and the fluorescence response recorded using a FLIPR instrument (Molecular Devices Corporation). To quantify antagonism of the agonist response, cells were preincubated with varying concentrations of test compound for 2-20 min and then exposed to 2 nM senktide, a concentration that alone elicits about an 70% maximal calcium response. The resulting data was analyzed using XLfit software (IDBS manufacturer) to determine $EC_{50}$ and $IC_{50}$ values.

The invention claimed is:

1. A compound that is 3-methanesulfonylamino-2-phenyl-quinoline-4-carboxylic acid ((S)-1-phenyl-propyl)-amide, or a pharmaceutically acceptable salt thereof.

2. A pharmaceutical composition comprising the compound according to claim 1 together with at least one pharmaceutically acceptable diluent, lubricant or carrier.

* * * * *